United States Patent [19]

Anshus

[11] 4,050,994

[45] Sept. 27, 1977

[54] RECOVERY OF 2-PYRROLIDONE FROM DILUTE ALKALINE SOLUTIONS

[75] Inventor: Byron E. Anshus, Orinda, Calif.

[73] Assignee: Chevron Research Company, San Francisco, Calif.

[21] Appl. No.: 745,501

[22] Filed: Nov. 26, 1976

[51] Int. Cl.[2] .................. B01D 3/34; C07D 207/12
[52] U.S. Cl. ........................... 203/35; 203/14; 203/47; 203/73; 260/78 P; 260/326.5 FN
[58] Field of Search ............. 203/14, 34, 35, 39, 203/47, 73, 91, 88; 260/78 P, 326.5 FN

[56] References Cited

U.S. PATENT DOCUMENTS

| | | | |
|---|---|---|---|
| 2,939,869 | 6/1960 | Carlson | 260/78 P |
| 3,248,388 | 4/1966 | Wintersberger et al. | 203/35 UX |
| 3,288,687 | 11/1966 | Zimmerli et al. | 203/35 |
| 3,290,329 | 12/1966 | Doerfel et al. | 260/326.5 FN |
| 3,597,330 | 8/1971 | Wegerech et al. | 203/35 |
| 3,681,293 | 8/1972 | Jarovitzky et al. | 260/78 P |
| 3,850,890 | 11/1974 | Ciaperoni | 260/78 P |
| 3,968,087 | 7/1976 | Choi | 260/78 P |

*Primary Examiner*—Wilbur L. Bascomb, Jr.
*Attorney, Agent, or Firm*—Dix A. Newell; S. Russell LaPaglia; T. G. DeJonghe

[57] ABSTRACT

A two-stage evaporative method for recovering polymerizable 2-pyrrolidone from alkaline aqueous solutions such as those obtained by washing the catalyst from an incompletely reacted polypyrrolidone polymerizate, includes the steps of neutralizing the base with mineral acid, removing most of the water in an initial reduced pressure evaporation and recovering the pyrrolidone from a salt/pyrrolidone slurry by vaporization under reduced pressure.

4 Claims, No Drawings

RECOVERY OF 2-PYRROLIDONE FROM DILUTE ALKALINE SOLUTIONS

BACKGROUND OF THE INVENTION

This invention relates to a process for the recovery of 2-pyrrolidone from an alkaline aqueous solution containing the same. More particularly, this invention relates to a process for the recovery of unreacted 2-pyrrolidone, of sufficiently high purity to be polymerizable with normal treatment, from the wash water used to remove the alkaline catalyst from an incompletely reacted polypyrrolidone polymerizate. 2-pyrrolidone has a normal boiling point of 245° C and is readily and completely miscible with water.

In polymerizing 2-pyrrolidone using an alkaline catalyst, the recovery of unreacted pyrrolidone may be accomplished by several methods all of which begin by washing the incompletely reacted polymerizate with water or a water-miscible solvent to extract the alkaline catalyst and unreacted pyrrolidone. The resulting alkaline aqueous pyrrolidone-containing solution may be directly distilled, but this is found to produce a gel-like residue which limits the recoverability of 2-pyrrolidone and furthermore, the alkali tends to hydrolyze the 2-pyrrolidone. Alternatively, the alkaline aqueous solution of 2-pyrrolidone may be separated into two phases, one of which is richer in 2-pyrrolidone, by the addition of certain inorganic salts; however, this does not solve the problem of complete recovery of 2-pyrrolidone. Furthermore, the phase-separation method was found to be particularly applicable to potassium-containing alkaline solutions and impractical for sodium-containing solutions.

BRIEF SUMMARY OF THE INVENTION

The two-stage evaporative process for the recovery of 2-pyrrolidone from alkaline aqueous solutions comprises the steps of adding a strong mineral acid such as sulfuric acid to said solution in amounts sufficient to provide a substantially neutralized or acidified solution of 3–7 pH, removing by evaporation a major amount of the water from said neutralized solution to provide a salt/2-pyrrolidone slurry, and recovering 2-pyrrolidone from said slurry by vaporization under a reduced pressure. Alternately, 2-pyrrolidone may be recovered by filtration of the salt/2-pyrrolidone slurry followed by evaporation of the filtrate.

DESCRIPTION OF PREFERRED EMBODIMENTS

In the process of the present invention, normally polymerizable 2-pyrrolidone is recovered from dilute alkaline aqueous wash solutions used to remove the alkaline catalyst from an incompletely reacted polypyrrolidone polymerizate. The solution contains about 10–50 weight percent 2-pyrrolidone and has a pH of about 12–13. Relatively pure 2-pyrrolidone is recovered by substantially neutralizing the alkaline solution with a strong mineral acid, such as sulfuric acid, to a pH of about 3–7, and preferably about 3–5, i.e., a neutral, or preferably acid, solution. The neutralized solution is then subjected to a first rapid evaporation, of the order of minutes to at most a few hours at atmospheric, but preferably under reduced pressure, preferably at about 25–100 mm Hg (torr). The first evaporation removes a major amount, preferably about 90 weight percent or more, of the water present in the neutralized solution, and most preferably about 98–99%. This first evaporation is preferably carried out at temperatures of about 50°–100° C, but in general less than about 120° C. Preferably a forced circulation evaporator is used.

The evaporation of this large quantity of water precipitates a substantial amount of solids, i.e., salts such as potassium sulfate, which are relatively insoluble in 2-pyrrolidone. Thus the product of the first evaporative step is normally a slurry of salts in 2-pyrrolidone and water. Furthermore, unless the evaporation is carried out substantially under these conditions, an appreciable amount, i.e. as much as 5 percent or more, of a benzene-insoluble organic residue is produced which effectively prevents the complete recovery of 2-pyrrolidone from the slurry in later steps of the process. The unsatisfactory slurry is observed to be "pasty". The residue is believed to comprise an oligomer or derivative of 2-pyrrolidone, such as gamma-aminobutyric acid.

In the process of the present invention the entire slurry, or the filtrate from the slurry, is directly subjected to a second evaporation at reduced pressure, i.e., most preferably about 3–5 torr, but preferably less than about 10 torr. The temperature of the slurry during the evaporative process is not critical, but is preferably about 100°–150° C and most preferably about 110° C. The vaporization is carried out until the solid residue is substantially dry. The second evaporation is preferably carried out in a thin-film dryer having at least about 3 square feet of evaporator surface per 100 pounds/hour of overhead.

The present process results in the recovery of more than 95% of the 2-pyrrolidone originally present in the dilute alkaline aqueous wash water, less than about 1–2% being lost as a benzene-insoluble residue on the solid salt residue. The recovered 2-pyrrolidone is of such high purity that it may be directly polymerized or preferably mixed with fresh 2-pyrrolidone for the normal preliminary purification prior to the making of catalysts and polymerization. This purification is normally carried out by distillation.

The present process has an additional advantage in that it has been found to destroy certain of the deleterious impurities which occur in 2-pyrrolidone, namely, and principally, butanediol. Butanediol is the major polymerization inhibitor found in 2-pyrrolidone made by certain procedures. It is not consumed in the polymerization reaction, so that continual recycling of unreacted 2-pyrrolidone would lead to the build-up of butanediol to an unacceptable level and eventual poisoning of the polymerization. The present process using sulfuric acid and acidified solutions of pH 3–5, carried out in repeated recycling of excess 2-pyrrolidone in incomplete polymerizations, results in a very limited build-up of butanediol to only about 0.02 mol percent based on total 2-pyrrolidone at each stage of repeated polymerization. Acidification of the alkaline aqueous solutions tends to destroy butanediol. Other impurities which occur in 2-pyrrolidone may be handled within the scope of the present invention, if necessary, by bleeding a 2–5% side-stream from the recycled 2-pyrrolidone and either discarding it or purifying it.

The process of the present invention is also applicable to the purification of crude, or semi-crude, 2-pyrrolidone which has been subjected to an alkali treatment. The present method has the further advantage of being applicable to sodium, potassium, ammonium and other alkaline aqueous 2-pyrrolidone solutions. It avoids hydrolysis of 2-pyrrolidone by the alkali and gel-formation during distillation of the alkaline solution.

The process of the present invention may comprise additional steps and treatments as are necessary, particularly for the treatment of crude pyrrolidone. For example, the 2-pyrrolidone vaporized from the slurry may be subjected to condensation in a partial condenser to achieve an extra stage of separation. 2-pyrrolidone may also be purified by recrystallization from water solutions.

EXEMPLIFICATION

EXAMPLE 1

2-pyrrolidone was incompletely polymerized to nylon-4 using potassium pyrrolidonate catalyst and carbon dioxide activator. The product was washed with water. Six thousand pounds of wash water containing 13 weight percent 2-pyrrolidone and 2 weight percent KOH was neutralized to pH 6.5 with concentrated sulfuric acid. Water was removed from the neutralized solution by evaporation at 50°-110° C and 50-100 torr over a 13 hour period. The resultant slurry contained about 80 weight percent organic material (including 2-pyrrolidone), 20 weight percent $K_2SO_4$ and less than 1 weight percent water. The slurry was fed into a heated thin film drier at 5 torr to recover a dry potassium sulfate bottoms product containing 2% organic residue and a polymerizable 2-pyrrolidone overhead.

EXAMPLE 2

As described in Example 1, 6000 pounds of wash water from the washing of incompletely polymerized 2-pyrrolidone and comprising 13 weight percent 2-pyrrolidone and 2 weight percent KOH was partially neutralized to pH 9 with concentrated sulfuric acid. The water was removed from the solution by evaporation at 50°-110° C and 50-100 torr over a 13-hour period. The resultant slurry contained about 80 weight percent organic material (including 2-pyrrolidone), 20% $K_2SO_4$ and less than 1% water. This slurry was fed to a heated thin film drier at 5 torr. The overhead product was found to be polymerizable 2-pyrrolidone. However, the potassium sulfate bottoms product contained 4% organic residue and was found to be "pasty" and not freely flowing.

EXAMPLE 3

A sample of the basic (pH 9) potassium sulfate-pyrrolidone slurry from Example 2 was filtered to recover a pyrrolidone-rich filtrate. The filter cake was quickly water-washed to recover the organic materials held on the filter cake. This wash filtrate was combined with the pyrrolidone-rich filtrate and charged to a flask. All volatile contents were evaporated at 1 torr at temperature up to 250° C. The residue was found to be "gummy" and hard to physically remove from the flask.

EXAMPLE 4

A sample of the basic (pH 9) potassium sulfate-pyrrolidone slurry from Example 2 was filtered to recover a pyrrolidone-rich filtrate. The filter cake was quickly water-washed to recover the organic material held on the filter cake. The wash filtrate was combined with the pyrrolidone-rich filtrate and charged to a flask. The contents were acidified to pH 6 with sulfuric acid and then all volatile components were evaporated at 1 torr at temperatures up to 250° C. The residue was a dry and free-flowing potassium sulfate. The difference between Examples 3 and 4 is attributed solely to the difference in pH of the solutions.

What is claimed is:

1. A process for the recovery of 2-pyrrolidone from alkaline aqueous solution, which comprises the steps of adding sulfuric acid to said solution in amounts sufficient to provide a neutralized or acidified solution of 3-7 pH, removing by a first evaporation a major amount of the water from said neutralized or acidified solution to provide a slurry comprising sulfate salt and 2-pyrrolidone, and recovering 2-pyrrolidone from said slurry by a second evaporation under reduced pressure.

2. The process for the recovery of 2-pyrrolidone from alkaline aqueous solution according to claim 1, which comprises the steps of adding sulfuric acid to said solution in amounts sufficient to provide a neutralized or acidified solution of 3-7 pH, removing by a first evaporation at 25-100 torr and less than about 120° C, a major amount of the water from said neutralized or acidified solution to provide a slurry comprising a sulfate salt and 2-pyrrolidone, and recovering 2-pyrrolidone from said slurry by a second evaporation under reduced pressure.

3. The process for the recovery of 2-pyrrolidone from alkaline aqueous solution according to claim 1, which comprises the steps of adding sulfuric acid to said solution in amounts sufficient to provide an acidified solution of 3-5 pH, removing by a first evaporation under reduced pressure at least about 90 weight percent of the water from said acidified solution to provide a slurry comprising a sulfate salt and 2-pyrrolidone, and recovering 2-pyrrolidone from said slurry by a second evaporation under reduced pressure of less than about 10 torr.

4. The process for the recovery of 2-pyrrolidone from alkaline aqueous solution according to claim 1, which comprises the steps of adding sulfuric acid to said solution in amounts sufficient to provide a neutralized or acidified solution of 3-7 pH, removing by a first evaporation at 25-100 torr and less than about 120° C, at least about 90 weight percent of the water from said neutralized or acidified solution to provide a slurry comprising a sulfate salt and 2-pyrrolidone, and recovering 2-pyrrolidone from said slurry by filtering or centrifuging said slurry and evaporating the filtrate or centrifugate under reduced pressure.

* * * * *